United States Patent [19]

Shioyama et al.

[11]  4,419,525

[45]  Dec. 6, 1983

[54] RECOVERY AND REJUVENATION OF WACKER-TYPE CATALYSTS

[75] Inventors: Tod K. Shioyama; Jim J. Straw, both of Bartlesville, Okla.

[73] Assignee: Phillips Petroleum Company, Bartlesville, Okla.

[21] Appl. No.: 357,101

[22] Filed: Mar. 11, 1982

[51] Int. Cl.³ .................... C07C 45/27; C07C 45/34; B01J 31/40; B01J 23/96

[52] U.S. Cl. .................................... 568/401; 502/22; 502/27; 568/359; 568/360; 568/475; 568/478

[58] Field of Search ............... 252/420, 414, 413, 412, 252/411 R; 568/401, 359, 360, 475, 478

[56] References Cited

U.S. PATENT DOCUMENTS

| 3,392,200 | 7/1968 | Vrbaski | 260/593 |
|---|---|---|---|
| 3,485,877 | 12/1969 | Hargis et al. | 568/475 |
| 3,607,948 | 2/1968 | Welton | 252/467 |
| 4,203,927 | 5/1980 | Stapp | 568/401 |
| 4,220,604 | 9/1980 | Stapp | 568/401 |
| 4,237,071 | 12/1980 | Stapp | 568/401 |
| 4,237,331 | 12/1980 | Stapp | 568/401 |
| 4,271,320 | 6/1981 | Tokitoh | 568/401 |

FOREIGN PATENT DOCUMENTS 1508331  4/1978  United Kingdom ................ 252/441

OTHER PUBLICATIONS

M. Cihova, M. Hrusovsky, J. Voitko and K. I. Matveev, "Catalytic Oxidation of Octene-1 in the Presence of Palladium(II) Salts and Heteropolyacids", *React. Kinet. Catal. Lett.*, vol. 16, No. 4, 383–386 (1981).

*Primary Examiner*—P. E. Konopka

[57] ABSTRACT

Wacker-type oxidation catalysts can be recovered and rejuvenated for further use by separating catalyst solids from the reaction mixture and, optionally, adjusting pH.

5 Claims, No Drawings

RECOVERY AND REJUVENATION OF WACKER-TYPE CATALYSTS

BACKGROUND OF THE INVENTION

The Wacker-type oxidation of ethylene to acetaldehyde using a palladium chloride/cupric chloride/hydrochloric acid catalyst in an aqueous solution has been modified and applied to the synthesis of methyl ketones from terminal olefins. However, major problems have been encountered in using the Wacker-type oxidation in the oxidation of higher olefins and internal olefins. One problem is that of reduced rates of reaction due to the low solubility of the olefin in the aqueous medium. Another major problem is the concomitant secondary oxidation of the ketone product which leads to poor selectivities and poor yield of desired product.

The solubility problems encountered in the Wacker-type oxidation of higher olefins have been at least partially solved by resorting to "phase transfer" techniques and the addition of a suitable surfactant. Thus, the prior art teaches that the reaction of the olefinic hydrocarbon reactant to be oxidized in the presence of free oxygen is preferably carried out in a multi-phase diluent system, preferably a two-phase system with one phase aqueous and the other organic. The catalysts known for this multi-phase process are Pd/Cu/alkali metal or alkaline earth metal chloride catalyst or Pd/Cu/boric acid catalyst with the palladium being either free palladium or a palladium compound and the copper component being either a cuprous or a cupric compound. It should also be noted that the HCl used in conventional Wacker oxidation reactions to maintain adequate conversion levels of the olefinic reactant has been eliminated as a component of the multi-phase process. An additional component of this multi-phase prior art reaction system is a suitable surfactant.

The cost and availability of the catalyst components make the consideration of catalyst recycle advisable. To this end, the development of a technique by which Wacker-type oxidation catalysts could be separated for reuse is desirable.

THE INVENTION

In accordance with this invention, used Wacker-type oxidation catalysts are recovered and regenerated for further oxidation reactions. Following reaction, the organic phase is separated from the catalyst-containing aqueous phase and the aqueous phase is treated so that the catalyst can be recycled.

The recovery and regeneration steps involved include:

(1) removing the organic phase from the reaction mixture to leave an aqueous phase, (2) removing water from the aqueous phase until substantially dry catalyst solids remain, (3) adding fresh water to the product of step (2) to yield a solution and (4) recycling the solution of step (3) to the reaction zone. In one embodiment, an acid addition is made to bring the catalyst solution to a pH of about 0.5 to 3.0 before recycling to the reaction zone.

ADVANTAGES

The regenerated catalysts of the invention can be reused many times in oxidation reactions with minimal effects on conversion and selectivity to carbonyl products. This means considerable savings in time and cost since the catalysts can be recovered and recycled in a simple fashion.

OBJECTS OF THE INVENTION

It is one object of the invention to produce a process whereby oxidation catalysts can be rejuvenated for reuse.

It is another object of the invention to produce a process in which the oxidation of olefins to ketones is carried out using regenerated catalysts.

DESCRIPTION OF THE INVENTION

The catalysts which are rejuvenated in accordance with the invention have palladium, heteropolyacid, and surfactant components. Generally, they are employed with a multi-component diluent system to oxidize olefinic reactants.

I. CATALYST SYSTEM

The catalyst utilized according to the instant invention for the oxidation of olefinic hydrocarbons to carbonyl compounds is made up of three components: (1) a palladium component, (2) a heteropolyacid component, and (3) a surfactant component. The use of (4) a boric acid component is optional.

(1) Palladium Component

The palladium component of the catalyst system of the instant invention can be any palladium-containing material whose properties render it suitable for use in Wacker or Wacker-type reactions. The palladium component of the invention can be palladium metal, e.g., finely divided palladium powder, or a palladium compound. Examples of suitable palladium compounds include allyl palladium chloride dimer [C$_3$H$_5$PdCl]$_2$, dichlorobis(triphenylphosphine)palladium(II), palladium(II) acetate, palladium(II) acetylacetonate, tetrakis(triphenylphosphine)palladium(O), palladium(II) chloride, palladium(II) iodide, palladium(II) nitrate, palladium(II) sulfate, and the like. Mixtures of the above palladium compounds can also be utilized as the palladium component of the instant catalyst system if so desired, thus providing a means to minimize the halide content of the catalyst system.

(2) Heteropolyacid Component

The heteropolyacid component of the catalyst system of the instant invention should have a redox potential in excess of 0.5 volt and contain at least two metallic species. It is preferred that it contain molybdenum and vanadium. Such preferred heteropolyacids are defined herein as iso-polymolybdates in which one or more of the molybdenum atoms are replaced by vanadium or an iso-polyvanadate in which one or more of the vanadium atoms are replaced by molybdenum.

The polyacid used contains vanadium atoms, for example from 1 to 8, more preferably 6 atoms, in a molecule, and molybdenum. Typical polyacids for use in the present invention are represented by the following general formula:

$$H_m[X_xMo_aV_bM_yO_z]$$

in which
X is B, Si, Ge, P, As, Se, Te or I;
M is W, Nb, Ta or Re;
m, a, b and z are integers;

x is zero (for mixed isopolyacids) or an integer (for hetero-polyacids); and y is zero or an integer such that $$6 \leq \frac{y + a + b}{z} \leq 12$$

and $m + Nx + 6a + 5b + N''y \leq 2z$
in which each of N and N' is the number of the group of the periodic table to which X and M respectively belong. Examples of typical heteropolyacids are as follows:

| Heteropolyacid | Redox potential, V |
|---|---|
| $H_9[TeMo_3V_3O_{24}]$ | +0.80 |
| $H_4[As_2Mo_{12}V_6O_{61}]$ | +0.65 |
| $H_3[AsMo_6V_6O_{40}]$ | +0.72 |
| $H_6[SiMo_{10}V_2O_{40}]$ | |
| $H_6[GeMo_{10}V_2O_{40}]$ | |
| $H_n[PMo_pV_qO_{40}]$*, for example: | |
| $H_4[PMo_{11}VO_{40}]$ | +0.65 |
| $H_5[PMo_{10}V_2O_{40}]$ | +0.70 |
| $H_6[PMo_9V_3O_{40}]$ | +0.72 |
| $H_7[PMo_8V_4O_{40}]$ | +0.75 |
| $H_8[PMo_7V_5O_{40}]$ | +0.76 |
| $H_9[PMo_6V_6O_{40}]$ | +0.77 |
| $H_{10}[PMo_5V_7O_{40}]$ | +0.79 |
| $H_{11}[PMo_4V_8O_{40}]$ | +0.80 |
| $H_5[Mo_rW_mV_2O_{40}]$** | |
| $H_9[PMo_3W_3V_6O_{40}]$ | +0.70 |

*in which $n = 3 + q$, $p = 12 - q$, $q = 1$ to 10
**in which $m = 2, 4, 6, 8$ and $r = 10 - m$.

The ratios of the various catalyst components can be expressed in terms of a molar ratio of heteropolyacid to palladium. The molar ratio of heteropolyacid component to palladium component in the instant catalyst system is broadly about 1/1 up to 50/1.

The amount of catalyst employed according to the instant invention can be expressed in terms of the molar ratio of olefinic hydrocarbon reactant to palladium component of the catalyst system. Broadly, the molar ratio of olefinic reactant to palladium component is from about 5/1 up to 1000/1 and preferably from about 10/1 up to 250/1.

(3) Surfactant Component

Generally, the surfactant component of the reaction system according to the instant invention comprises one or more compounds which exhibit surface-active properties—i.e., surfactants. However, the term "surfactant" encompasses a very broad class of compounds, and it has been discovered that not all surfactants are suitable for use in the instant invention. Nevertheless, for convenience and simplicity, the suitable compounds that can be employed according to the instant invention and described more fully below will be termed surfactants herein. At the present time, it is not known whether, in the catalyst and process of the invention, these compounds function as phase-transfer catalysts, such as is taught in the art, or whether they function as micellar catalysts, a feature also disclosed in the prior art. Because of this uncertainty in the mode of action of these compounds in the instant invention and for convenience, the following compounds will merely be described herein as surfactants.

A preferred surfactant for use in the reaction system of the instant invention is selected from one of the five following groups:

(A) Quaternary ammonium salts of the general formula $(R''')_4N^+X^-$ wherein $R'''$ is an alkyl radical of from 1 to 20 carbon atoms and wherein the total number of carbon atoms in said quaternary ammonium salt is from 8 to 30 carbon atoms broadly and preferably from 16 to 22 carbon atoms; and wherein X is selected from the group consisting of $Br^-$, $Cl^{31}$, $I^-$, $F^-$, $R'''CO_2^-$, $QSO_3^-$, $BF_4^-$, and $HSO_4^-$, wherein Q is an aryl, alkaryl or arylalkyl radical of 6 to 10 carbon atoms. It will be noted that a variety of anions are suitable as the $X^{31}$ component of the quaternary ammonium salts.

Useful quaternary ammonium salts according to the general formula given above include cetyltrimethylammonium bromide, hexadecyltrimethylammonium bromide, tetraheptylammonium bromide, cetyltrimethylammonium stearate, benzyltributylammonium chloride, benzyltriethylammonium bromide, benzyltrimethylammonium bromide, phenyltrimethylammonium bromide, phenyltrimethylammonium iodide, tetrabutylammonium bromide, tetrabutylammonium chloride, tetrabutylammonium hydrogen sulfate, tetrabutylammonium iodide, tetraethylammonium bromide, tetrabutyl ammonium fluoride, and tetrabutylammonium tetrafluoroborate.

(B) Alkali metal alkyl sulfates of the general formula $R'^vOSO_3M$, wherein $R'^v$ is an alkyl radical having from 10 to about 20 carbon atoms and wherein M is an alkali metal. Examples of suitable compounds according to the general formula for the alkali metal alkyl sulfates include lithium decylsulfate, potassium dodecylsulfate, sodium dodecylsulfate, sodium hexadecylsulfate, potassium hexadecylsulfate, rubidium dodecylsulfate, cesium dodecylsulfate, sodium octadecylsulfate, potassium octadecylsulfate, potassium eicosylsulfate, sodium eicosylsulfate and the like.

(C) Alkali metal salts of alkanoic acids of the general formula $R'^vCO_2M$, wherein $R'^v$ and M have the same meaning as given above for the compounds of (B). Examples of suitable alkali metal salts of alkanoic acids include lithium decanoate, sodium dodecanoate, potassium dodecanoate, rubidium dodecanoate, cesium dodecanoate, sodium hexadecanoate, potassium hexadecanoate, sodium octadecanoate, potassium octadecanoate, sodium eicosanoate, potassium eicosanoate, and the like.

(D) Alkali metal salts of alkaryl sulfonic acids of the general formula

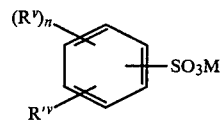

wherein $R'^v$ and M have the same meaning as given and wherein $R^v$ is an alkyl radical of 1 to 4 carbon atoms and wherein n is 0 or an integer of from 1 to 4. Typical compounds within the (D) group include sodium dodecylbenzenesulfonate, potassium dodecylbenzenesulfonate, lithium dodecylbenzenesulfonate, sodium tetradecylbenzenesulfonate, potassium hexadecylbenzenesulfonate, rubidium dodecylbenzenesulfonate, cesium dodecylbenzenesulfonate, sodium octadecylbenzenesulfonate, potassium octadecylbenzenesulfonate, sodium eicosylbenzenesulfonate, potassium dodecyltoluenesulfonate, sodium dodecylxylenesulfonate and the like.

(E) 1-Alkyl pyridinium salts of the general formula

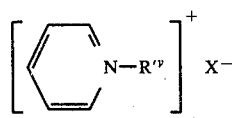

wherein R'ᵛ and X⁻ have the same meanings as described above. Examples of suitable 1-alkyl pyridinium salts are 1-dodecylpyridinium para-toluenesulfonate, 1-dodecylpyridinium chloride, 1-hexadecylpyridinium chloride, 1-hexadecylpyridinium para-toluenesulfonate, 1-decylpyridinium chloride, 1-hexadecylpyridinium bromide, 1-tetradecylpyridinium chloride, 1-octadecylpyridinium chloride, 1-eicosylpyridinium chloride, 1-octadecylpyridinium benzenesulfonate, and the like.

The amount of surfactant compound selected from groups (A) through (E) which is utilized according to be utilized to form the organic phase according to the instant invention.

Generally speaking, suitable compounds can be found in the classes of compounds described as aliphatic hydrocarbons, aromatic hydrocarbons or alkylsubstituted aromatic hydrocarbons, halogenated aromatic compounds, and esters of aromatic carboxylic acids although the latter may be less preferred because of a tendency toward hydrolysis of the ester group in certain instances. In addition, it has been found that compounds such as nitrobenzene and benzonitrile, commonly utilized as solvents for many organic reactions, show a definite inhibitory effect on the reaction of the instant invention presumably by complexing of one or more catalyst components.

Suitable organic diluents include cyclohexane, hexane, octane, decane, dodecane, tetradecane, hexadecane, benzene, toluene, chlorobenzene, methylbenzoabove. Thus, the reaction of the instant invention is carried out in the presence of free oxygen. The oxygen may be supplied to the reaction mixture essentially as pure oxygen or in admixture with other gases which are essentially inert to the reaction conditions. Air can be utilized as a source of oxygen for the oxidation reaction of this invention.

As is generally true for most oxidation reactions, the reaction of the instant invention can be exothermic and thus some care should be exercised in controlling the amount of oxygen present in the reaction system. For this reason, and also to improve control of the temperature of the reaction, it is preferred to add oxygen or the gaseous mixture containing oxygen to the reaction zone incrementally so that explosive oxygen concentrations do not develop. The pressure of oxygen utilized for the instant invention can be from about 2 up to 250 psig and, preferably, from about 10 to 100 psig above the autogenous pressure at the temperature utilized.

IV. OLEFINIC HYDROCARBON REACTANT

The olefinic hydrocarbon reactant which is oxidized according to the process of the instant invention can be selected from the groups consisting of acyclic olefinic compounds containing from 2–20 carbon atoms per molecule and having 1, 2, or 3 olefinic carbon-carbon double bonds per molecule and cyclic olefinic compounds containing from 5–20 carbon atoms per molecule and having 1, 2, or 3 olefinic carbon-carbon double bonds per molecule. Within the limitations described above, suitable olefinic hydrocarbon reactants can be represented by the general formula RCH=CHR' wherein R and R' are selected from the group consisting of hydrogen, alkyl, alkenyl, alkadienyl, cycloalkyl, cycloalkenyl, and cycloalkadienyl radicals and wherein R can be the same or different from R' and wherein R and R' taken together can form an alkylene or alkenylene or alkadienylene radical thus forming a cyclic system. The term "olefinic carbon-carbon double bond" as used herein is not meant to include those carbon-carbon double bonds which are part of an aromatic carbocyclic system of alternating single and double bonds.

Examples of suitable monoolefinic compounds are ethylene, propylene, 1-butene, 2-butene, 1-pentene, 2-pentene, 1-hexene, 2-hexene, 1-octene, 1-decene, 1-dodecene, 1-hexadecene, 1-octadecene, 1-eicosene, vinyl cyclohexane, cyclopentene, cyclohexene, cycloheptene, cyclooctene, cyclododecene, 3,3-dimethyl-1-butene, and the like.

Examples of suitable diolefinic compounds are 1,3-butadiene, 1,3-pentadiene, 1,5-hexadiene, 4-vinylcyclohexene, 1,5-cyclooctadiene, 1,9-decadiene, 1,7-octadiene, 1,3-cycloheptadiene, and the like.

Suitable triolefinic compounds include 1,5,9-cyclododecatriene, cycloheptatriene, 1,6-diphenyl-1,3,5hexatriene, and the like.

While the double bond unsaturation can be internal or non-terminal, it is preferred that at least one olefinic carbon-carbon double bond be in the terminal position. That is, the preferred olefinic reactant has at least one terminal olefinic or vinyl group. Mixtures of olefinic reactants can be employed.

V. REACTION CONDITIONS

The particular temperature employed may be dependent somewhat on the olefinic hydrocarbon reactant. For example, at relatively high temperatures, a lower molecular weight olefinic hydrocarbon reactant may tend to be very insoluble in the aqueous phase of the two-phase system of the instant invention, thus causing a reduced conversion of the olefinic hydrocarbon reactant. On the other hand, a higher molecular weight olefinic reactant may be able to tolerate a higher reaction temperature and still maintain a reasonable degree of solubility in the aqueous phase and thus achieve a good degree of conversion at the higher temperature. The temperature utilized in the instant invention is broadly from about 20° to 200° C. and preferably from about 60° to 150° C. Most preferably it lies between about 70° and 100°C.

The time employed for the reaction according to the instant invention can vary over a wide range and will, to some extent, depend on the desired degree of conversion of the olefinic hydrocarbon reactant. Generally, a time period such as from 30 minutes to 8 hours will be employed in the instant invention, preferably 1 to 3 hours.

Because the oxidation reaction according to the instant invention is carried out in the presence of a diluent system comprising at least two liquid phases, it is expected that good stirring will be beneficial. Conventional means of achieving good agitation and contact between the liquid phases can be employed.

The charge order of the reaction components and catalyst components is not critical in the process of the instant invention. However, the presence of oxygen in the reaction mixture prior to heating of the mixture to the desired reaction temperature appears to promote higher selectivity to the desired carbonyl compound.

Reaction vessels and conduits utilized in the process of the instant invention should, of course, be able to withstand the oxidizing conditions which are present. For this reason, glass-lined, tantalum, titanium or Hastelloy C-clad vessels and conduits are recommended for use in the process of this invention.

VI. CATALYST RECOVERY AND REJUVENATION

A variety of methods can be utilized to recover the products, unreacted olefinic hydrocarbon starting materials, and the catalyst in the aqueous phase in the instant invention. One preferred method of catalyst recovery and rejuvenation involves flash distillation. During this distillation, volatile organics, such as unreacted olefins, volatile products, and small amounts of organic solvent(s), are removed. Typical distillation temperatures will lie between about 50° and 100° C., at pressures between about 200 mm and 760 mm Hg. The liquids which remain are phase separated. The organic solvent thus recovered is suitable for recycle and the aqueous phase is treated in or on a device which will strip the catalyst solids to substantial dryness. Devices which employ reduced pressure or vacuum, e.g. rotary evaporators, are contemplated. Other suitable devices include standard distillation still, wiped film evaporater, or the like. It is preferred that the catalyst solids be substantially dehydrated.

Following the stripping operation, the catalyst is mixed with fresh water. The resultant water/catalyst solution is used as is or its pH is adjusted to a value of about 0.5 to 3.0 preferably about 0.7 to 2.0 via the addition of acid. Suitable acids include HCl and $H_2SO_4$. Sulfuric acid is preferred. The redissolved catalyst is then ready for recycle to the reaction zone and reuse.

In one embodiment, reaction was carried out at 80° C. for 2 hours with 30 psig initial $O_2$ pressure and using a PdCl$_2$/H$_9$[PMo$_6$V$_6$O$_{40}$]/cetyltrimethylammonium bromide oxidation catalyst. When the reaction was complete, the reactor contents were subjected to a flash distillation to remove all volatile materials. The aqueous phase was placed on a rotary evaporator and stripped to dryness under reduced pressure. Fresh water (100 g) was added to the residual solids (original pH 2.50) and the pH adjusted to 1.97 by adding H$_2$SO$_4$. This redissolved catalyst was ready for reuse with no further handling.

When the catalyst is reused for several reactions, it is sometimes desirable to replenish one or more of the catalyst components between cycles. Additions of 0.0001–0.001 moles, or about 10% of the original charge of the palladium, heteropolyacid, and/or the surfactant are typical.

Another method of treating the reaction mixture is to contact the entire mixture with a lower alkane such as n-pentane, then separate the aqueous phase from the organic phase, with subsequent fractional distillation of the organic phase to recover the products and any unreacted olefinic hydrocarbon reactants. The aqueous phase can be treated and recycled to the reaction zone as described above.

Another method of reaction mixture workup involves admixture of the reaction mixture with a saturated aqueous sodium chloride solution followed by extraction of the mixture into diethyl ether. The ether extract can then be distilled or treated in such a manner as to remove the ether leaving the organic residue containing the product and any unreacted olefinic hydrocarbon reactant. Said residue can then be subjected to fractional distillation procedures to recover the various reaction components.

VII. PRODUCT UTILITY

As indicated earlier, the reaction of the instant invention provides a process for the conversion of olefinic hydrocarbon reactants to carbonyl compounds. Said carbonyl compounds are ketones, except for the case of ethylene oxidation which yields acetaldehyde. If the olefinic hydrocarbon reactant contains two carbon-carbon double bonds, the product can be an unsaturated monoketone or diketone. Furthermore, the unsaturated monoketone can be recycled to the reaction zone for conversion to the diketone. Similarly a triolefinic reactant can be converted to intermediates such as unsaturated mono- or diketones and ultimately to a triketone. Ketones from the olefinic hydrocarbon reactants described in part IV above have generally well-known utilities. For instance, they can be utilized as solvents (e.g., methyl ethyl ketone) or as intermediates in the synthesis of other chemical compounds (e.g., pinacolone).

VIII. EXAMPLES

In all of the runs that are described in the following examples, the reaction vessel utilized was a 300 cc Hastelloy C Magnedrive stirred tank reactor sold by Autoclave Engineers or a 500 mL Fischer-Porter compatibility aerosol bottle. The autoclave was heated by an electric heater and controlled by a Thermoelectric 400 temperature controller. The Fisher-Porter bottles were fitted with pressure gauges, vent and chargelines through which oxygen could be added continuously or incrementally. The oxygen line to the reaction vessel was fitted with the appropriate check valves and flame arrestor. The bottle was heated in an ethylene glycol bath, and monitored on an Acromag by a thermocouple placed in the glycol bath. All temperatures recorded are in °C. The bottle contents were stirred by a magnetic stirrer.

For autoclave runs, the reactor was charged with the catalyst system, the diluents, and then sealed. Thirty psig oxygen pressure was introduced to pressure test the reactor, then vented. The olefinic reactant was then charged, while autoclave stirring was begun to aid olefin dissolution in the organic diluent. Thirty psig oxygen pressure was again introduced and the autoclave heated to the desired reaction temperature before the oxgyen pressure was adjusted to the desired operating pressure. The reaction was allowed to take-up oxygen on demand for the duration of the reaction in order to maintain the desired pressure. For runs carried out in the Fischer-Porter bottles, the catalyst, diluents, and olefinic reactant were charged. The bottle was assembled with the proper fittings, placed in the ethylene glycol bath, and stirring begun. An initial pressure of 30 psig oxygen was introduced, the reaction mixture heated to the desired reaction temperature, then oxygen pressure raised to the desired reaction value. As above, the system was allowed to take-up oxygen on demand to maintain the desired operating pressure throughout the reaction.

After the desired reaction time had elapsed the reaction was cooled to room temperature before excess oxygen was vented. The combined organic and aqueous phases were subjected to conventional fractional distillation to recover volatile materials (starting material, products and by-products). After distillation, the residual materials were phase separated, decane solvent being recycled to the reactor while the aqueous phase was subjected to further treatment to regenerate the catalyst components therein. All samples were analyzed by gas-liquid phase chromatography.

EXAMPLE I

Preparation of the Phospho-6-molybdo-6-vanadic acid 45.5 g Na$_3$PO$_4$.12H$_2$O (0.12 mol), 103.6 g MoO$_3$ (0.72 mol), 42.0 g V$_2$O$_5$ (0.23 mol) and 22.4 Na$_2$CO$_3$.10H$_2$O (0.08 mol) were dissolved in 600 mL H$_2$O. The solution was heated to boiling and stirred vigorously for 40 minutes. The solution gradually turned an intense brownish-red. The solution volume was reduced to 150 mL by evaporation, then allowed to cool to room temperature. The pH of the solution was adjusted to 1.00 with concentrated sulfuric acid, the solution was then filtered and set aside for use as a component in the inventive oxidation process.

EXAMPLE II

A series of 2-butene oxidations were carried out using a 500 mL Fischer-Porter bottle containing 100 mL water, 100 g (137 mL) decane, 0.05 mol phospho-6-molybdo-6-vanadic acid, and reagents in the amounts tabulated in Table I. Reactions were carried out for 3 hrs. at 80° and 80 psig according to the general procedure set forth above. Decane and water phases recovered upon workup were returned to the reactor with no further treatment, fresh butene was charged, and the next run begun.

TABLE I

| Run # | PdCl$_2$, mol | CTMAB*, mol | Butene Charged, mol | Butene Conversion, mol % | Selectivity MEK, mol % |
|---|---|---|---|---|---|
| 1 | 0.01 | 0.004 | 0.40 | 96.8 | 81.0 |
| 2 | " | " | 0.45 | 76.2 | 87.6 |
| 3 | " | " | 0.49 | 56.1 | 90.8 |
| 4 | " | " | 0.41 | 47.8 | 87.1 |

*cetyltrimethylammonium bromide

This example demonstrates the reduced activity of the palladium-heteropolyacid-surfactant of the catalyst system over several reaction cycles in the absence of catalyst regeneration.

EXAMPLE III

A series of 2-butene oxidations were carried out using a 500 mL Fischer-Porter bottle containing 100 mL water, 100 g (137 mL) decane, 0.05 mol phospho-6-molybdo-6-vanadic acid, 0.01 mol palladium chloride and 0.004 mol CTMAB. Reactions were carried out for 3 hrs. at 80° and 80 psig according to the general procedure set forth above. Decane phase recovered upon workup was set aside for return to the reactor after the water phase was subjected to regeneration as follows:

The pH of the aqueous phase was adjusted to 0.1 with concentrated H$_2$SO$_4$. The Fischer-Porter bottle containing the acidic aqueous material was sealed and pressured to 100 psig with O$_2$. The vessel was then heated as indicated in Table II. After the requisite time for treatment, the vessel was cooled, recycle decane phase added and a fresh charge of 2-butene introduced.

TABLE II

| Run # | Butene Charged, mol | Butene Conversion, mol % | Selectivity to MEK, mol % | Regeneration Conditions | | |
|---|---|---|---|---|---|---|
| | | | | Temp, °C. | Time, Hrs. | Maximum Pressure |
| 1 | 0.51 | 47.8 | 86.2 | 160 | 3 | 145 |
| 2 | 0.49 | 81.1 | 91.2 | 110 | 4 | 110 |
| 3 | 0.49 | 62.3 | 87.6 | 115 | 4 | 120 |
| 4 | 0.43 | 85.9 | 86.9 | 114 | 3 | 115 |
| 5 | 0.44 | 66.9 | 87.7 | 118 | 3* | 120 |
| 6 | 0.45 | 77.5 | 89.2 | 114 | 3 | 115 |
| 7 | 0.43 | 51.5 | 91.2 | 118 | 5 | 110 |
| 8 | 0.38 | 52.0 | 88.5 | — | — | — |

*Prior to oxidative regeneration, aqueous phase was evaporated to dryness on the rotary evaporator, then residual solids were redissolved in fresh water.

This example demonstrates the reduced activity of the palladium heteropolyacid-surfactant catalyst system over several reaction cycles even with an oxidative treatment of catalyst between runs.

EXAMPLE IV

The procedure described in example III for the oxidation of 2-butene with recycle of catalyst was repeated with a fresh catalyst charge. Thus, 100 mL water, 100 g (137 mL) decane, 0.05 mol phospho-6-molybdo-6-vanadic acid, 0.01 mol palladium chloride and 0.004 mol CTMAB were loaded into a 500 mL Fischer-Porter bottle. As above, reactions were carried out for 3 hrs. at 80° and 80 psig.

TABLE III

| Run # | Butene Charged, mol | Butene Conversion, mol % | Selectivity to MEK, mol % | Regeneration Conditions | | |
|---|---|---|---|---|---|---|
| | | | | Temp, °C. | Time, Hrs. | Maximum Pressure |
| 1 | 0.46 | 56.9 | 89.5 | 115 | 3 | 100 |
| 2 | 0.46 | 55.5 | 86.9 | 115 | 3 | 100 |
| 3 | 0.44 | 77.6 | 86.5 | 107 | 3 | 100 |
| 4 | 0.39 | 65.4 | 85.8 | 104 | 3 | 100 |
| 5 | 0.40 | 66.5 | 86.5 | 108 | 3 | 100 |
| 6 | 0.43 | 77.9 | 90.6 | 108 | 3 | 100 |
| 7 | 0.50 | 59.4 | 95.8 | — | — | — |

This sample demonstrates the reduced activity of the palladium-heteropolyacid-surfactant catalyst system over several reaction cycles even with an oxidative treatment of catalyst between runs.

EXAMPLE V

A series of 1-butene oxidations were carried out utilizing the same catalyst charge for numerous recycles, with intermittent replenishing of catalyst components (as noted in Table IV, below) to compensate for handling losses associated with catalyst recycle. All reactions were carried out using a 500 mL Fischer-Porter bottle containing 100 mL water, 100 g (137 mL) decane and reagents in the amounts tabulated in Table IV. Reactions were carried out for 2 hours at 80° and 100 psig according to the general procedure set forth above. Decane phase recovered upon workup was returned to the reactor for the next run, and the water phase was evaporated to dryness, the residue redissolved in deionized water, H$_2$SO$_4$ added to adjust pH to 1.9 and the resulting solution was then recycled to the reactor.

TABLE IV

| Run # | PdCl$_2$, mol | Heteropolyacid, mol | CTMAB, mol | Butene Charged, mol | Butene Conversion, mol % | Selectivity to MEK, mol % |
|---|---|---|---|---|---|---|
| 1 | 0.01 | 0.05 | 0.004 | 0.45 | 56.0 | 92.7 |
| 2 | * | * | * | 0.45 | 65.0 | 92.8 |
| 3 | +0.0001 | * | +.00003 | 0.46 | 70.5 | 91.4 |
| 4 | * | * | * | 0.43 | 80.2 | 90.5 |
| 5 | +0.0001 | * | +.00003 | 0.46 | 77.6 | 92.3 |
| 6 | * | * | * | 0.46 | 80.5 | 90.0 |
| 7 | +0.0001 | * | +.00003 | 0.46 | 79.3 | 91.9 |
| 8 | * | * | * | 0.45 | 80.0 | 91.2 |
| 9 | +0.0001 | * | +.00003 | 0.48 | 88.4 | 90.6 |
| 10 | * | * | * | 0.44 | 89.0 | 90.0 |
| 11 | +0.0001 | * | +.00003 | 0.46 | 89.8 | 93.0 |
| 12 | * | * | * | 0.45 | 88.0 | 93.6 |
| 13 | * | * | * | 0.44 | 92.6 | 92.0 |
| 14 | * | * | * | 0.45 | 75.3 | 95.5 |
| 15 | * | * | * | 0.45 | 85.7 | 93.7 |

*Same catalyst charge recycled from previous run.

This example demonstrates the excellent performance of the palladium-heteropolyacid-surfactant oxidation system over numerous reaction cycles when regenerated according to the inventive procedure.

EXAMPLE VI

A series of 2-butene oxidations were carried out utilizing the same catalyst charge for numerous recycles, occasionally recharging catalyst components (as noted in Table V below) to compensate for handling losses. All reactions were carried out using a 500 mL Fischer-Porter bottle containing 100 mL water, 100 g (137 mL) decane, and reagents in the amounts tabulated in Table V. Reactions were carried out for 2 hours at 80° and 100 psig according to the general procedure set forth above. Decane and water phases were recycled in the inventive manner as described in Example V.

TABLE V

| Run # | PdCl$_2$, mol | Heteropolyacid, mol | CTMAB, mol | Butene Charged, mol | Butene Conversion, mol % | Selectivity to MEK, mol % |
|---|---|---|---|---|---|---|
| 1 | 0.01 | 0.05 | 0.004 | 0.47 | 64.2 | 84.5 |
| 2 | +.0001 | * | +.00003 | 0.46 | 56.4 | 87.7 |
| 3 | * | * | * | 0.45 | 80.2 | 87.5 |
| 4 | * | * | * | 0.48 | 68.0 | 90.1 |
| 5 | +.0001 | * | +.00003 | 0.49 | 65.5 | 90.2 |
| 6 | * | * | * | 0.48 | 69.7 | 89.9 |
| 7 | +.0001 | * | +.00003 | 0.45 | 82.3 | 89.0 |
| 8 | * | * | * | 0.44 | 78.7 | 89.6 |

*Same catalyst charge recycled from previous run.

This example demonstrates the excellent performance of the palladium-heteropolyacid-surfactant oxidation system over numerous reaction cycles when regenerated according to the inventive procedure.

EXAMPLE VII

A series of 1-butene oxidations were carried out utilizing the same catalyst charge for numerous recycles, with intermittent replenishing of catalyst components (as noted in Table VI below) to compensate for handling losses associated with catalyst recycle. All reactions were carried out in a 500 mL Fischer-Porter bottle containing 100 mL water, 100 g (137 mL) decane, and reagents in the amounts tabulated in Table VI. Reactions were carried out for 1 hour at 80° and 100 psig according to the general procedure set forth above. Decane and water phases were recycled in the inventive manner as described in Example V.

TABLE VI

| Run # | PdCl$_2$, mol | Heteropolyacid, mol | CTMAB, mol | Butene Charged, mol | Butene Conversion, mol % | Selectivity to MEK, mol % |
|---|---|---|---|---|---|---|
| 1 | 0.01 | 0.05 | 0.004 | 0.35 | 47.9 | 92.7 |
| 2 | * | * | * | 0.35 | 41.4 | 94.5 |
| 3 | +.001 | * | +.0003 | 0.37 | 65.7 | 91.4 |
| 4 | * | * | * | 0.37 | 55.8 | 91.1 |
| 5 | +.001 | * | +.0003 | 0.38 | 62.7 | 91.9 |
| 6 | * | * | * | 0.35 | 67.5 | 92.2 |
| 7 | +.001 | * | +.0003 | 0.34 | 66.6 | 93.3 |
| 8 | * | * | * | 0.36 | 73.6 | 91.7 |
| 9 | +.001 | * | +.0003 | 0.38 | 75.3 | 93.3 |
| 10 | * | * | * | 0.37 | 69.5 | 92.8 |
| 11 | * | * | * | 0.38 | 67.9 | 93.3 |
| 12 | * | * | * | 0.37 | 50.5 | 96.4 |
| 13 | * | * | * | 0.38 | 68.3 | 94.5 |
| 14 | * | * | * | 0.38 | 62.2 | 95.9 |

*Same catalyst charge recycled from previous run.

This example demonstrates the excellent performance of the palladium-heteropolyacid-surfactant oxidation system over numerous reaction cycles when regenerated according to the inventive procedure.

EXAMPLE VIII

A series of 1-butene oxidations were carried out utilizing the same catalyst charge for numerous recycles, occasionally recharging palladium (as noted in Table VII below) to compensate for handling losses. All reactions were carried out using a 500 mL Fischer-Porter bottle containing 100 mL water, 100 g (137 mL) decane, 0.05 mol heteropolyacid, 0.25 mol H$_3$BO$_3$, and palladium in the amounts tabulated in Table VII. Reactions were carried out for 2 hours at 80° and 100 psig according to the general procedure set forth above. Decane and water phases were recycled in the inventive manner as described in Example V.

TABLE VII

| Run # | PdCl$_2$, mol | Butene Charged, mol | Butene Conversion, mol % | Selectivity to MEK, mol % |
|---|---|---|---|---|
| 1 | 0.01 | 0.45 | 66.7 | 92.0 |
| 2 | * | 0.44 | 65.7 | 97.5 |
| 3 | +.001 | 0.45 | 82.0 | 97.0 |
| 4 | * | 0.45 | 59.3 | 99.1 |
| 5 | +.001 | 0.46 | 54.7 | 99.1 |
| 6 | * | 0.45 | 30.6 | 97.4 |

*Same catalyst charge recycled from previous run.

These experiments demonstrate the operability of the process of this invention for the oxidation of 1-butene to methyl ethyl ketone in the presence of the palladium-heteropolyacid-boric acid catalyst system in two-phase medium over several catalyst recycles. High butene conversions with excellent selectivity to MEK are maintained through several recycles of the catalyst.

EXAMPLE IX

A series of 2-butene oxidations were carried out utilizing the same catalyst charge for numerous recycles, occasionally recharging palladium (as noted in Table VIII below) to compensate for handling losses. All reactions were carried out using a 500 mL Fischer-Porter bottle containing 100 mL water, 100 g (137 mL) decane, 0.05 mol heteropolyacid, 0.25 mol $H_3BO_3$, and palladium in the amounts tabulated in Table VIII. Reactions were carried out for 2 hours at 80° and 100 psig according to the general procedure set forth above. Decane and water phases were recycled in the inventive manner as described in Example V.

TABLE VIII

| Run # | $PdCl_2$, mol | Butene Charged, mol | Butene Conversion, mol % | Selectivity to MEK, mol % |
|---|---|---|---|---|
| 1 | .01 | 0.47 | 87.5 | 86.8 |
| 2 | * | 0.44 | 79.3 | 88.7 |
| 3 | +.001 | 0.45 | 73.0 | 92.9 |
| 4 | * | 0.45 | 63.8 | 95.3 |
| 5 | +.001 | 0.45 | 44.1 | 97.4 |
| 6 | * | 0.45 | 40.8 | 96.3 |

*Same catalyst charge recycled from previous run.

These experiments demonstrate the operability of the process of this invention for the oxidation of 2-butene to methyl ethyl ketone in the presence of the palladium-heteropolyacid-boric acid catalyst in two-phase medium over several catalyst recycles. High butene conversions with excellent selectivity to MEK are maintained through several recycles of the catalyst.

EXAMPLE X

A series of 2-butene oxidations were carried out utilizing the same catalyst charge for numerous recycles, occasionally recharging catalyst components (as noted in Table IX below) to compensate for handling losses. All reactions were carried out using a 500 mL Fischer-Porter bottle containing 100 mL water, 100 g (137 mL) decane, 0.05 mol heteropolyacid, 0.25 mol $H_3BO_3$, and palladium and surfactant in the amounts tabulated in Table IX. Reactions were carried out for 2 hours at 80° and 100 psig according to the general procedure set forth above. Decane and water phases were recycled in the inventive manner as described in Example V.

TABLE IX

| Run # | $PdCl_2$, mol | CTMAB, mol | Butene Charged, mol | Butene Conversion, mol % | Selectivity to MEK, mol % |
|---|---|---|---|---|---|
| 1 | 0.01 | 0.004 | 0.52 | 51.9 | 91.3 |
| 2 | * | * | 0.42 | 59.8 | 90.4 |
| 3 | +.001 | +.0003 | 0.52 | 51.4 | 87.7 |
| 4 | * | * | 0.47 | 58.9 | 91.1 |
| 5 | +.001 | +.0003 | 0.44 | 77.3 | 89.3 |
| 6 | * | * | 0.45 | 69.0 | 90.3 |

*Same catalyst charge recycled from previous run.

These experiments demonstrate the operability of the process of this invention for the oxidation of 2-butene to methyl ethyl ketone in the presence of the palladium-heteropolyacid-boric acid-surfactant catalyst system in two-phase medium over several catalyst recycles. Excellent butene conversions with high selectivity to MEK are maintained through several recycles of the catalyst.

Reasonable variations, such as those which occur to the skilled artisan, can be made herein without departing from the scope of the invention.

We claim:

1. A process for the recovery and rejuvenation for reuse of a catalyst useful for the oxidation of olefins to ketones which catalyst contains a palladium component, a heteropolyacid component, and a surfactant component following its use to catalyze the oxidation of an olefin to a ketone in a reaction zone to produce a reaction mixture which contains an organic phase and an aqueous phase, which process includes the essential steps of:

(1) removing the organic phase from the reaction mixture to leave the aqueous phase,
    (2) removing water from the aqueous phase until substantially dry catalyst solids remain,
    (3) adding water to the product of step (2) to yield a solution, and
    (4) recycling the solution of step (3) to the reaction zone.

2. The process of claim 1 which includes the step of (5) adjusting the pH of the solution from step (4) to a pH of about 0.5 to 3.0 before it is recycled to the reaction zone.

3. The process of any one of claims 1 or 2 wherein the catalyst also contains one or more boric acid components.

4. A process for the oxidation of olefins to ketones which process comprises the step of contacting an olefin with a catalyst which contains a palladium component, a heteropolyacid component, and a surfactant component, wherein the catalyst has been recovered following its use to produce a reaction mixture which contains an organic phase and an aqueous phase and has been rejuvenated by a process which includes the essential steps (1) removing the organic phase from the reaction mixture to leave an aqueous phase,
    (2) recovering water from the aqueous phase until substantially dry catalyst solids remain,
    (3) adding water to the product of step (2) to yield a solution, and
    (4) recycling the solution of step (3) to the reaction zone.

5. The process of claim 4 wherein the catalyst also contains one or more boric acid components.

* * * * *